(12) United States Patent   (10) Patent No.: US 8,403,927 B1
Shingleton                   (45) Date of Patent:    Mar. 26, 2013

(54) VASECTOMY DEVICES AND METHODS

(76) Inventor: William Bruce Shingleton, Evans, GA (US)

( * ) Notice: Subject to any disclaimer, the term of this patent is extended or adjusted under 35 U.S.C. 154(b) by 0 days.

(21) Appl. No.: 13/440,618

(22) Filed: Apr. 5, 2012

(51) Int. Cl.
    A61B 18/12 (2006.01)
(52) U.S. Cl. .................................................. 606/49
(58) Field of Classification Search .............. 606/27, 606/34, 41, 50–52, 49
    See application file for complete search history.

(56) References Cited

U.S. PATENT DOCUMENTS

| | | |
|---|---|---|
| 1,798,902 A | 3/1931 | Raney |
| 3,011,684 A | 12/1961 | Cornell |
| 3,353,491 A | 11/1967 | Bastian |
| 3,517,128 A | 6/1970 | Hines |
| 3,597,124 A | 8/1971 | Adams |
| 3,901,241 A | 8/1975 | Allen, Jr. |
| 3,974,833 A | 8/1976 | Durden, III |
| 4,011,872 A | 3/1977 | Komiya |
| 4,034,762 A | 7/1977 | Cosens et al. |
| 4,085,756 A | 4/1978 | Weaver |
| 4,103,688 A | 8/1978 | Edwards |
| 4,138,205 A | 2/1979 | Wallach |
| 4,187,057 A | 2/1980 | Xanthopoulos |
| 4,196,724 A | 4/1980 | Wirt et al. |
| 4,269,174 A | 5/1981 | Adair |
| 4,311,154 A | 1/1982 | Sterzer et al. |
| 4,315,510 A | 2/1982 | Kihn |
| 4,411,266 A | 10/1983 | Cosman |
| 4,423,812 A | 1/1984 | Sato |
| 4,493,319 A | 1/1985 | Polk et al. |
| 4,532,924 A | 8/1985 | Auth et al. |
| 4,552,516 A | 11/1985 | Stanley |
| 4,565,200 A | 1/1986 | Cosman |
| 4,568,255 A | 2/1986 | Lavender et al. |
| 4,673,393 A | 6/1987 | Suzuki et al. |
| 4,674,506 A | 6/1987 | Alcond |
| 4,705,041 A | 11/1987 | Kim |
| 4,708,604 A | 11/1987 | Kidera |
| 4,813,855 A | 3/1989 | Leveen et al. |
| 4,832,688 A | 5/1989 | Sagae et al. |
| 4,878,492 A | 11/1989 | Sinofsky et al. |
| 4,878,493 A * | 11/1989 | Pasternak et al. ............... 607/99 |

(Continued)

FOREIGN PATENT DOCUMENTS

| | | |
|---|---|---|
| DE | 3838840 | 5/1990 |
| DE | 4303882 | 8/1994 |

(Continued)

OTHER PUBLICATIONS

Advisory Action for U.S. Appl. No. 10/273,900 dated Nov. 29, 2006.

(Continued)

*Primary Examiner* — Michael Peffley
*Assistant Examiner* — Daniel Fowler
(74) *Attorney, Agent, or Firm* — Jenkins, Wilson, Taylor & Hunt, P.A.

(57) ABSTRACT

Devices and methods for cauterizing a tubular vessel are disclosed. A device for cauterizing a tubular vessel can include a hand piece, a tip portion provided at an operative end of the hand piece, one or more probes extending from the tip portion, one or more grasping arms extending beyond the tip portion and movable to grasp a target tissue positioned at or near the tip portion, and a power supply configured to supply energy to the one or more probes.

19 Claims, 3 Drawing Sheets

U.S. PATENT DOCUMENTS

| | | |
|---|---|---|
| 4,901,737 A | 2/1990 | Toone |
| 4,906,203 A | 3/1990 | Margrave |
| 4,907,589 A | 3/1990 | Cosman |
| 4,920,982 A | 5/1990 | Goldstein |
| 4,925,376 A | 5/1990 | Kahler |
| 4,943,290 A | 7/1990 | Rexroth et al. |
| 4,947,842 A | 8/1990 | Marchosky |
| 4,955,377 A | 9/1990 | Lennox et al. |
| 4,966,597 A | 10/1990 | Cosman |
| 4,976,711 A | 12/1990 | Parins |
| 4,994,033 A | 2/1991 | Shockey et al. |
| 5,002,558 A | 3/1991 | Klein et al. |
| 5,007,897 A | 4/1991 | Kalb et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,049,132 A | 9/1991 | Shaffer et al. |
| 5,057,107 A | 10/1991 | Parins |
| 5,078,717 A | 1/1992 | Parins |
| 5,083,565 A | 1/1992 | Parins |
| 5,084,044 A | 1/1992 | Quint |
| 5,088,522 A | 2/1992 | Rath et al. |
| 5,088,979 A | 2/1992 | Filipi et al. |
| 5,092,841 A | 3/1992 | Spears |
| 5,094,233 A | 3/1992 | Brennan |
| 5,100,423 A | 3/1992 | Fearnot |
| 5,100,429 A | 3/1992 | Sinofsky et al. |
| 5,102,390 A | 4/1992 | Crittenden et al. |
| 5,106,360 A | 4/1992 | Ishiwara et al. |
| 5,110,270 A | 5/1992 | Morrick |
| 5,122,137 A | 6/1992 | Lennox |
| 5,125,928 A | 6/1992 | Parins |
| 5,156,151 A | 10/1992 | Imran |
| 5,188,596 A | 2/1993 | Condon et al. |
| 5,190,540 A | 3/1993 | Lee |
| 5,190,541 A | 3/1993 | Abele |
| 5,197,963 A | 3/1993 | Parins |
| 5,197,964 A | 3/1993 | Parins |
| 5,199,951 A | 4/1993 | Spears |
| 5,205,287 A | 4/1993 | Erbel et al. |
| 5,209,776 A | 5/1993 | Bass et al. |
| 5,213,580 A | 5/1993 | Slepian et al. |
| 5,215,103 A | 6/1993 | Desai |
| 5,215,450 A | 6/1993 | Tamari |
| 5,219,355 A | 6/1993 | Parodi et al. |
| 5,226,908 A * | 7/1993 | Yoon .......................... 606/141 |
| 5,232,444 A | 8/1993 | Just et al. |
| 5,236,413 A | 8/1993 | Feiring |
| 5,239,982 A | 8/1993 | Trauthen |
| 5,242,441 A | 9/1993 | Avitall |
| 5,254,126 A | 10/1993 | Filipi et al. |
| 5,256,138 A | 10/1993 | Burek et al. |
| 5,257,451 A | 11/1993 | Edwards |
| 5,263,493 A | 11/1993 | Avitall |
| 5,273,535 A | 12/1993 | Edwards et al. |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,278,201 A | 1/1994 | Dunn et al. |
| 5,281,217 A | 1/1994 | Edwards |
| 5,281,218 A | 1/1994 | Imran |
| 5,286,254 A | 2/1994 | Shapland et al. |
| 5,290,286 A | 3/1994 | Parins |
| 5,292,321 A | 3/1994 | Lee |
| 5,293,869 A | 3/1994 | Edwards |
| 5,309,910 A | 5/1994 | Edwards |
| 5,313,943 A | 5/1994 | Houser |
| 5,314,466 A | 5/1994 | Stern |
| 5,316,020 A | 5/1994 | Truffer |
| 5,318,531 A | 6/1994 | Leone |
| 5,322,503 A | 6/1994 | Desai |
| 5,324,284 A | 6/1994 | Imran |
| 5,324,288 A | 6/1994 | Billings et al. |
| 5,328,467 A | 7/1994 | Edwards |
| 5,328,471 A | 7/1994 | Slepian et al. |
| 5,334,196 A | 8/1994 | Scott |
| 5,334,201 A | 8/1994 | Cowan |
| 5,336,222 A | 8/1994 | Durgin, Jr. et al. |
| 5,340,290 A | 8/1994 | Clemens |
| 5,342,181 A | 8/1994 | Schock et al. |
| 5,342,357 A | 8/1994 | Nardella et al. |
| 5,345,936 A | 9/1994 | Pomeranz et al. |
| 5,348,554 A | 9/1994 | Imran |
| 5,349,825 A | 9/1994 | Duke et al. |
| 5,354,279 A | 10/1994 | Hofling |
| 5,363,861 A | 11/1994 | Edwards |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards |
| 5,370,678 A | 12/1994 | Edwards et al. |
| 5,383,876 A | 1/1995 | Nardella |
| 5,383,917 A | 1/1995 | Desai |
| 5,385,544 A | 1/1995 | Edwards |
| 5,388,972 A | 2/1995 | Calhoun et al. |
| 5,397,339 A | 3/1995 | Desai |
| 5,398,683 A | 3/1995 | Edwards |
| 5,400,783 A | 3/1995 | Pomeranz et al. |
| 5,401,272 A | 3/1995 | Perkins |
| 5,403,311 A | 4/1995 | Rowe et al. |
| 5,405,322 A | 4/1995 | Lennox et al. |
| 5,409,000 A | 4/1995 | Imran |
| 5,409,453 A | 4/1995 | Lundquist |
| 5,409,483 A | 4/1995 | Campbell et al. |
| 5,415,657 A | 5/1995 | Taymor-Luria |
| 5,421,819 A | 6/1995 | Edwards et al. |
| 5,423,744 A | 6/1995 | Gencheff et al. |
| 5,423,808 A | 6/1995 | Edwards |
| 5,423,811 A | 6/1995 | Imran |
| 5,423,812 A | 6/1995 | Ellman et al. |
| 5,428,486 A | 6/1995 | Nagase |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,447,417 A | 9/1995 | Kuhl et al. |
| 5,448,990 A | 9/1995 | De Faria-Correa |
| 5,454,782 A | 10/1995 | Perkins |
| 5,456,662 A | 10/1995 | Edwards |
| 5,456,682 A | 10/1995 | Edwards et al. |
| 5,458,568 A | 10/1995 | Racchini et al. |
| 5,458,596 A | 10/1995 | Lax |
| 5,458,597 A | 10/1995 | Edwards |
| 5,464,395 A | 11/1995 | Faxon et al. |
| 5,464,404 A | 11/1995 | Abela et al. |
| 5,465,717 A | 11/1995 | Imran et al. |
| 5,470,308 A | 11/1995 | Edwards et al. |
| 5,470,309 A | 11/1995 | Edwards |
| 5,471,982 A | 12/1995 | Edwards et al. |
| 5,472,441 A | 12/1995 | Edwards |
| 5,484,400 A | 1/1996 | Edwards et al. |
| 5,485,849 A | 1/1996 | Panescu et al. |
| 5,486,161 A | 1/1996 | Lax |
| 5,490,984 A | 2/1996 | Freed |
| 5,496,271 A | 3/1996 | Burton et al. |
| 5,496,311 A | 3/1996 | Abele et al. |
| 5,498,238 A | 3/1996 | Shapland et al. |
| 5,500,012 A | 3/1996 | Brucker et al. |
| 5,505,728 A | 4/1996 | Ellman |
| 5,505,730 A | 4/1996 | Edwards |
| 5,507,743 A | 4/1996 | Edwards |
| 5,509,419 A | 4/1996 | Edwards |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards |
| 5,531,677 A | 7/1996 | Lundquist |
| 5,536,240 A | 7/1996 | Edwards |
| 5,536,267 A | 7/1996 | Edwards et al. |
| 5,540,655 A | 7/1996 | Edwards et al. |
| 5,542,915 A | 8/1996 | Edwards |
| 5,542,916 A | 8/1996 | Hirsch |
| 5,545,161 A | 8/1996 | Imran |

| | | | | | | |
|---|---|---|---|---|---|---|
| 5,545,171 | A | 8/1996 | Sharkey | 5,871,483 | A | 2/1999 | Jackson et al. |
| 5,545,193 | A | 8/1996 | Fleischman | 5,873,877 | A | 2/1999 | McGaffigan et al. |
| 5,545,434 | A | 8/1996 | Huarng | 5,882,346 | A | 3/1999 | Pomeranz et al. |
| 5,549,108 | A | 8/1996 | Edwards | 5,891,135 | A | 4/1999 | Jackson |
| 5,549,644 | A | 8/1996 | Lundquist | 5,891,141 | A | 4/1999 | Rydell |
| 5,554,110 | A | 9/1996 | Edwards | 5,921,954 | A | 7/1999 | Mohr, Jr. et al. |
| 5,556,377 | A | 9/1996 | Rosen | 5,957,920 | A | 9/1999 | Baker |
| 5,558,672 | A | 9/1996 | Edwards et al. | 5,964,755 | A | 10/1999 | Edwards |
| 5,558,673 | A | 9/1996 | Edwards | 5,964,782 | A | 10/1999 | Lafontaine et al. |
| 5,562,720 | A | 10/1996 | Stern et al. | 5,964,791 | A | 10/1999 | Bolmsjo |
| 5,569,241 | A | 10/1996 | Edwards | 5,968,041 | A | 10/1999 | Edwards |
| 5,569,242 | A | 10/1996 | Lax et al. | 5,989,284 | A | 11/1999 | Laufer |
| 5,571,116 | A | 11/1996 | Bolanos et al. | 6,002,968 | A | 12/1999 | Edwards |
| 5,575,788 | A | 11/1996 | Baker et al. | 6,006,755 | A | 12/1999 | Edwards |
| 5,582,589 | A | 12/1996 | Edwards et al. | 6,009,877 | A | 1/2000 | Edwards |
| 5,588,432 | A | 12/1996 | Crowley | 6,015,407 | A | 1/2000 | Rieb et al. |
| 5,588,960 | A | 12/1996 | Edwards et al. | 6,016,437 | A | 1/2000 | Tu et al. |
| 5,591,125 | A | 1/1997 | Edwards et al. | 6,035,238 | A | 3/2000 | Ingle et al. |
| 5,591,199 | A | 1/1997 | Porter et al. | 6,036,689 | A | 3/2000 | Tu et al. |
| 5,595,183 | A | 1/1997 | Swanson et al. | 6,044,846 | A | 4/2000 | Edwards |
| 5,599,294 | A | 2/1997 | Edwards et al. | 6,044,847 | A | 4/2000 | Carter et al. |
| 5,599,295 | A | 2/1997 | Rosen et al. | 6,045,496 | A | 4/2000 | Pacella et al. |
| 5,599,307 | A | 2/1997 | Bacher et al. | 6,048,329 | A | 4/2000 | Thompson et al. |
| 5,599,345 | A | 2/1997 | Edwards | 6,056,744 | A | 5/2000 | Edwards |
| 5,599,346 | A | 2/1997 | Edwards et al. | 6,056,747 | A | 5/2000 | Saadat et al. |
| 5,601,591 | A | 2/1997 | Edwards et al. | 6,071,230 | A | 6/2000 | Henalla |
| 5,607,389 | A | 3/1997 | Edwards et al. | 6,073,052 | A | 6/2000 | Zelickson et al. |
| 5,607,422 | A | 3/1997 | Smeets et al. | 6,077,257 | A | 6/2000 | Edwards et al. |
| 5,609,151 | A | 3/1997 | Mulier et al. | 6,081,749 | A | 6/2000 | Ingle et al. |
| 5,624,439 | A | 4/1997 | Edwards et al. | 6,091,995 | A | 7/2000 | Ingle et al. |
| 5,630,794 | A | 5/1997 | Lax et al. | 6,092,528 | A | 7/2000 | Edwards |
| 5,630,812 | A | 5/1997 | Ellman et al. | 6,099,526 | A | 8/2000 | Whayne |
| 5,662,609 | A | 9/1997 | Slepian | 6,106,521 | A | 8/2000 | Blewett et al. |
| 5,667,488 | A | 9/1997 | Lundquist et al. | 6,139,569 | A | 10/2000 | Ingle et al. |
| 5,667,518 | A | 9/1997 | Pannell | 6,142,993 | A | 11/2000 | Whayne |
| 5,672,153 | A | 9/1997 | Lax et al. | 6,156,032 | A | 12/2000 | Lennox |
| 5,674,191 | A | 10/1997 | Edwards et al. | 6,156,060 | A | 12/2000 | Roy et al. |
| 5,681,277 | A | 10/1997 | Edwards et al. | 6,164,921 | A | 12/2000 | Moubayed et al. |
| 5,681,308 | A | 10/1997 | Edwards et al. | 6,165,172 | A | 12/2000 | Farley et al. |
| 5,683,384 | A | 11/1997 | Gough et al. | 6,168,594 | B1 | 1/2001 | Lafontaine |
| 5,685,839 | A | 11/1997 | Edwards et al. | 6,179,824 | B1 | 1/2001 | Eggers et al. |
| 5,688,266 | A | 11/1997 | Edwards et al. | 6,179,831 | B1 | 1/2001 | Bliweis |
| 5,688,490 | A | 11/1997 | Tournier et al. | 6,190,382 | B1 | 2/2001 | Ormsby et al. |
| 5,697,281 | A | 12/1997 | Eggers et al. | 6,197,022 | B1 | 3/2001 | Baker |
| 5,702,438 | A | 12/1997 | Avitall | 6,200,333 | B1 | 3/2001 | Laufer |
| 5,707,349 | A | 1/1998 | Edwards | 6,216,027 | B1 | 4/2001 | Willis et al. |
| 5,709,224 | A | 1/1998 | Behl et al. | 6,216,704 | B1 | 4/2001 | Ingle et al. |
| 5,709,539 | A | 1/1998 | Hammer et al. | 6,236,891 | B1 | 5/2001 | Ingle et al. |
| 5,715,817 | A | 2/1998 | Stevens-Wright et al. | 6,241,753 | B1 | 6/2001 | Knowlton |
| 5,718,702 | A | 2/1998 | Edwards | 6,254,586 | B1 | 7/2001 | Mann et al. |
| 5,720,718 | A | 2/1998 | Rosen et al. | 6,254,598 | B1 | 7/2001 | Edwards et al. |
| 5,722,975 | A | 3/1998 | Edwards et al. | 6,258,087 | B1 | 7/2001 | Edwards et al. |
| 5,728,094 | A | 3/1998 | Edwards | 6,273,886 | B1 | 8/2001 | Edwards et al. |
| 5,730,719 | A | 3/1998 | Edwards | 6,283,987 | B1 | 9/2001 | Laird et al. |
| 5,732,698 | A | 3/1998 | Swanson et al. | 6,283,989 | B1 | 9/2001 | Laufer |
| 5,738,096 | A | 4/1998 | Ben-Haim | 6,292,700 | B1 | 9/2001 | Morrison et al. |
| 5,738,114 | A | 4/1998 | Edwards | 6,322,584 | B2 | 11/2001 | Ingle et al. |
| 5,741,225 | A | 4/1998 | Lax et al. | 6,325,798 | B1 | 12/2001 | Edwards et al. |
| 5,743,870 | A | 4/1998 | Edwards | 6,338,726 | B1 | 1/2002 | Edwards et al. |
| 5,743,904 | A | 4/1998 | Edwards | 6,355,031 | B1 | 3/2002 | Edwards et al. |
| 5,746,224 | A | 5/1998 | Edwards | 6,358,245 | B1 | 3/2002 | Edwards et al. |
| 5,749,846 | A | 5/1998 | Edwards et al. | 6,402,744 | B2 | 6/2002 | Edwards et al. |
| 5,752,813 | A | 5/1998 | Tyner et al. | 6,409,723 | B1 | 6/2002 | Edwards |
| 5,762,626 | A | 6/1998 | Lundquist et al. | 6,416,504 | B2 | 7/2002 | Mosel et al. |
| 5,769,846 | A | 6/1998 | Edwards et al. | 6,423,058 | B1 | 7/2002 | Edwards et al. |
| 5,772,255 | A | 6/1998 | Osborne et al. | 6,425,853 | B1 | 7/2002 | Edwards |
| 5,785,642 | A | 7/1998 | Wallace et al. | 6,425,854 | B1 | 7/2002 | Galt et al. |
| 5,797,903 | A | 8/1998 | Swanson et al. | 6,425,877 | B1 | 7/2002 | Edwards |
| 5,800,482 | A | 9/1998 | Pomeranz et al. | 6,428,538 | B1 | 8/2002 | Blewett et al. |
| 5,800,484 | A | 9/1998 | Gough et al. | 6,440,127 | B2 | 8/2002 | McGovern et al. |
| 5,807,333 | A | 9/1998 | Osborne et al. | 6,440,128 | B1 | 8/2002 | Edwards et al. |
| 5,813,411 | A | 9/1998 | Van Bladel et al. | 6,447,505 | B2 | 9/2002 | McGovern et al. |
| 5,823,197 | A | 10/1998 | Edwards | 6,463,331 | B1 | 10/2002 | Edwards |
| 5,827,273 | A | 10/1998 | Edwards | 6,464,689 | B1 | 10/2002 | Qin et al. |
| 5,830,213 | A | 11/1998 | Panescu et al. | 6,464,697 | B1 | 10/2002 | Edwards et al. |
| 5,836,874 | A | 11/1998 | Swanson et al. | 6,470,219 | B1 | 10/2002 | Edwards et al. |
| 5,843,016 | A | 12/1998 | Lugnani et al. | 6,478,775 | B1 | 11/2002 | Galt et al. |
| 5,860,974 | A | 1/1999 | Abele | 6,480,746 | B1 | 11/2002 | Ingle et al. |
| 5,868,708 | A | 2/1999 | Hart et al. | 6,517,534 | B1 | 2/2003 | McGovern et al. |

| | | | |
|---|---|---|---|
| 6,544,226 B1 | 4/2003 | Gaiser et al. | |
| 6,547,776 B1 | 4/2003 | Gaiser et al. | |
| 6,579,266 B2 | 6/2003 | Mosel et al. | |
| 6,589,238 B2 | 7/2003 | Edwards et al. | |
| 6,599,256 B1 | 7/2003 | Acker et al. | |
| 6,613,047 B2 | 9/2003 | Edwards | |
| 6,626,901 B1 * | 9/2003 | Treat et al. | 606/29 |
| 6,645,201 B1 | 11/2003 | Utley et al. | |
| 6,666,848 B2 | 12/2003 | Stone | |
| 6,685,623 B2 | 2/2004 | Presthus et al. | |
| 6,692,490 B1 | 2/2004 | Edwards | |
| 6,699,243 B2 | 3/2004 | West et al. | |
| 6,733,495 B1 | 5/2004 | Bek et al. | |
| 6,743,165 B2 | 6/2004 | Mosel et al. | |
| 6,743,197 B1 | 6/2004 | Edwards | |
| 6,743,226 B2 | 6/2004 | Cosman et al. | |
| 6,749,607 B2 | 6/2004 | Edwards et al. | |
| 6,783,523 B2 | 8/2004 | Qin et al. | |
| 6,790,207 B2 | 9/2004 | Utley et al. | |
| 6,802,841 B2 | 10/2004 | Utley et al. | |
| 6,821,276 B2 | 11/2004 | Lambrecht et al. | |
| 6,827,713 B2 | 12/2004 | Bek et al. | |
| 6,830,052 B2 | 12/2004 | Carter et al. | |
| 6,836,688 B2 | 12/2004 | Ingle et al. | |
| 6,840,954 B2 | 1/2005 | Dietz et al. | |
| 6,852,110 B2 | 2/2005 | Roy et al. | |
| 6,866,663 B2 | 3/2005 | Edwards et al. | |
| 6,882,885 B2 | 4/2005 | Levy, Jr. et al. | |
| 6,976,492 B2 | 12/2005 | Ingle et al. | |
| 6,994,704 B2 | 2/2006 | Qin et al. | |
| 7,022,105 B1 | 4/2006 | Edwards | |
| 7,052,453 B2 | 5/2006 | Presthus et al. | |
| 7,077,841 B2 | 7/2006 | Gaiser et al. | |
| 7,160,270 B2 | 1/2007 | West et al. | |
| 7,160,294 B2 | 1/2007 | Croft | |
| 7,165,551 B2 | 1/2007 | Edwards et al. | |
| 7,179,219 B2 | 2/2007 | Matlock | |
| 7,184,827 B1 | 2/2007 | Edwards | |
| 7,223,267 B2 | 5/2007 | Isola et al. | |
| 7,251,531 B2 | 7/2007 | Mosher et al. | |
| 7,291,129 B2 | 11/2007 | Li et al. | |
| 7,306,591 B2 | 12/2007 | Thomas et al. | |
| 7,315,762 B2 | 1/2008 | Mosher et al. | |
| 7,317,949 B2 | 1/2008 | Morrison et al. | |
| 7,326,207 B2 | 2/2008 | Edwards | |
| 7,326,235 B2 | 2/2008 | Edwards | |
| 7,329,254 B2 | 2/2008 | West et al. | |
| 7,422,587 B2 | 9/2008 | Bek et al. | |
| 7,462,179 B2 | 12/2008 | Edwards et al. | |
| 7,468,060 B2 | 12/2008 | Utley et al. | |
| 7,476,242 B2 | 1/2009 | Matlock | |
| 7,536,225 B2 | 5/2009 | Spraker et al. | |
| 7,615,049 B2 | 11/2009 | West et al. | |
| 7,648,500 B2 | 1/2010 | Edwards et al. | |
| 7,722,338 B2 | 5/2010 | Nordell et al. | |
| 8,177,781 B2 | 5/2012 | Thomas et al. | |
| 2005/0234443 A1 * | 10/2005 | Rioux et al. | 606/41 |
| 2005/0288664 A1 | 12/2005 | Ford et al. | |
| 2006/0058780 A1 | 3/2006 | Edwards | |
| 2006/0149300 A1 | 7/2006 | Jessen et al. | |
| 2006/0155261 A1 | 7/2006 | Bek et al. | |
| 2006/0177328 A1 | 8/2006 | Nordell et al. | |
| 2006/0205996 A1 | 9/2006 | Presthus et al. | |
| 2007/0050001 A1 | 3/2007 | Luttich et al. | |
| 2007/0112340 A1 | 5/2007 | Thomas et al. | |
| 2008/0105265 A1 | 5/2008 | Pannell | |
| 2010/0049186 A1 | 2/2010 | Ingle et al. | |

FOREIGN PATENT DOCUMENTS

| | | |
|---|---|---|
| EP | 0139607 A1 | 5/1985 |
| EP | 0608609 B1 | 9/2001 |
| GB | 2069063 | 2/1981 |
| GB | 2269538 | 2/1994 |
| JP | 02-121675 | 5/1990 |
| JP | 04-246367 | 9/1992 |
| JP | 2000-342598 | 12/2000 |
| JP | 2001-514921 | 9/2001 |
| JP | 2002-503512 | 2/2002 |
| WO | WO 91/01773 A1 | 2/1991 |
| WO | WO 92/10142 A1 | 6/1992 |
| WO | WO 93/08755 A1 | 5/1993 |
| WO | WO 94/10925 A1 | 5/1994 |
| WO | WO 94/21165 A1 | 9/1994 |
| WO | WO 94/21178 A1 | 9/1994 |
| WO | WO 94/22366 A1 | 10/1994 |
| WO | WO 94/26178 A1 | 11/1994 |
| WO | WO 95/08289 | 3/1995 |
| WO | WO 95/18575 | 7/1995 |
| WO | WO 95/19142 | 7/1995 |
| WO | WO 95/25472 | 9/1995 |
| WO | WO 96/00042 | 1/1996 |
| WO | WO 96/16606 | 6/1996 |
| WO | WO 96/29946 | 10/1996 |
| WO | WO 97/06857 | 2/1997 |
| WO | WO 97/32532 | 9/1997 |
| WO | WO 97/43971 | 11/1997 |
| WO | WO 99/44522 | 9/1999 |
| WO | WO 00/62696 | 10/2000 |
| WO | WO 00/66052 | 11/2000 |
| WO | WO 01/06942 | 2/2001 |
| WO | WO 01/22897 | 4/2001 |
| WO | WO 01-34018 | 5/2001 |
| WO | WO 02/28475 | 4/2002 |

OTHER PUBLICATIONS

Advisory Action for U.S. Appl. No. 11/431,213 dated Apr. 14, 2010.
Final Office Action for U.S. Appl. No. 10/207,689 dated Jan. 17, 2007.
Final Office Action for U.S. Appl. No. 10/273,900 dated Aug. 4, 2006.
Final Office Action for U.S. Appl. No. 10/769,153 dated Jun. 27, 2007.
Final Office Action for U.S. Appl. No. 11/056,086 dated Jan. 13, 2009.
Final Office Action for U.S. Appl. No. 11/207,677 dated May 14, 2010.
Final Office Action for U.S. Appl. No. 11/431,213 dated Feb. 3, 2010.
Final Office Action for U.S. Appl. No. 12/494,871 dated Apr. 30, 2012.
Non-Final Office Action for U.S. Appl. No. 10/207,689 dated May 4, 2005.
Non-Final Office Action for U.S. Appl. No. 10/207,689 dated Jul. 17, 2006.
Non-Final Office Action for U.S. Appl. No. 10/273,900 dated Nov. 10, 2005.
Non-Final Office Action for U.S. Appl. No. 10/273,900 dated Jan. 29, 2007.
Non-Final Office Action for U.S. Appl. No. 10/769,153 dated Jan. 9, 2007.
Non-Final Office Action for U.S. Appl. No. 11/056,086 dated May 13, 2008.
Non-Final Office Action for U.S. Appl. No. 11/056,086 dated Jun. 19, 2009.
Non-Final Office Action for U.S. Appl. No. 11/207,677 dated Jun. 2, 2009.
Non-Final Office Action for U.S. Appl. No. 11/207,677 dated Dec. 29, 2009.
Non-Final Office Action for U.S. Appl. No. 11/431,213 dated Apr. 14, 2009.
Non-Final Office Action for U.S. Appl. No. 11/431,213 dated Feb. 23, 2011.
Non-Final Office Action for U.S. Appl. No. 12/494,871 dated Oct. 21, 2011.
Non-Final Office U.S. Appl. No. 11/207,677 dated Oct. 28, 2010.
Notice of Allowance for U.S. Appl. No. 10/207,689 dated Jun. 26, 2007.
Notice of Allowance for U.S. Appl. No. 10/273,900 dated Aug. 9, 2007.

Notice of Allowance for U.S. Appl. No. 10/769,153 dated Sep. 11, 2007.
Notice of Allowance for U.S. Appl. No. 11/056,086 dated Jan. 13, 2010.
Notice of Allowance for U.S. Appl. No. 11/431,213 dated Jan. 13, 2012.

International Search Report and Written Opinion for Application No. PCT/US2012/042430 dated Dec. 3, 2012.
US 5,401,172, 03/1995, Perkins (withdrawn)

* cited by examiner

US 8,403,927 B1

VASECTOMY DEVICES AND METHODS

TECHNICAL FIELD

The subject matter disclosed herein relates generally to devices and methods for sterilizing a male patient. More particularly, the subject matter disclosed herein relates to vasectomy devices and methods for supplying RF energy to ablate the vas deferens of a male patient.

BACKGROUND

Male sterilization is generally accomplished by vasectomy in which the ducts that carry sperm out of the testes (i.e., the vas deferens) are surgically interrupted by ligation and/or by cauterization, thereby stopping the flow of sperm from the testicle to the prostate gland. This procedure requires surgical opening of the scrotum. Ideally, a vasectomy is an outpatient procedure that is desirably completed with mild discomfort for the patient. The patient should then be capable of resuming his normal activities within a reasonable time frame. The majority of cases have this degree of successful results and limited aftereffects.

In a significant number of instances, however, prolonged exploration and manipulation accompanied by excessive discomfort both intraoperatively and postoperatively can make the results less than desirable. Complications can arise at least in part because scrotal tissue is highly elastic. Whereas a small amount of bleeding is quickly stopped by the tension that develops in non-elastic tissue, elastic tissue offers little pressure to slow the loss of blood and fluid. Thus, even the slightest amount of persistent bleeding can cause tremendously large hematomas. As a result, and in addition to causing discomfort, the healing process is slowed because of the prolonged time required to reabsorb these fluids and cells, increasing the opportunity for bacterial colonization.

In addition, another concern for the surgeon is the elusiveness of the vas deferens. This structure cannot be seen until the later stages of the procedure and must be identified by palpation. Once identified and delivered into the operative field, it must be held in place by some means of fixation. Even a momentary release of the vas allows it to immediately return to within the spermatic cord, from which it must again be extricated. Furthermore, the injection of a local anesthetic into the scrotal skin and the area surrounding the vas makes palpation of the structure difficult. Loss of fixation of the vas can result in the need for increased dissection, and manipulation can cause increased bleeding and swelling.

Even the most experienced vasectomy surgeons occasionally encounter these problems. As a result, it would be desirable for a system and method for performing a vasectomy to alleviate these complications. Specifically, it would be desirable for a system and method that allows a medical professional to securely and controllably holding the vas in place and to sterilize a male patient without incising the wall of the patient's scrotum.

SUMMARY

In accordance with this disclosure, devices and methods for cauterizing a tubular vessel are provided. As an example and in one aspect, a device for cauterizing a tubular vessel is provided. The device can comprise a hand piece, a tip portion provided at an operative end of the hand piece, one or more probes extending from the tip portion, one or more grasping arms extending beyond the tip portion and movable to grasp a target tissue positioned at or near the tip portion, and a power supply configured to supply energy to the one or more probes.

In another aspect, a device for cauterizing a tubular vessel can comprise a hand piece, a tip portion selectively connectable to an operative end of the hand piece, one or more probes extending from the tip portion, one or more grasping arms connected to the tip portion and extending beyond the tip portion, and a radio frequency energy generator configured to supply radio frequency energy to the one or more probes. Again, the one or more grasping arms can be movable to grasp a target tissue positioned at or near the tip portion.

In yet another aspect and in one example, a method for cauterizing a tubular vessel is provided. The method can comprise providing a device comprising a hand piece, a tip portion provided at an operative and of the hand piece, one or more probes extending from the tip portion, and one or more grasping arms extending beyond the tip portion. The method can further comprise positioning the device near to or against a physical body containing a tubular vessel, grasping the tubular vessel using the one or more grasping arms, moving the one or more probes into contact with the tubular vessel, and providing energy to the one or more probes to cauterize the tubular vessel.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

Figure 1A:
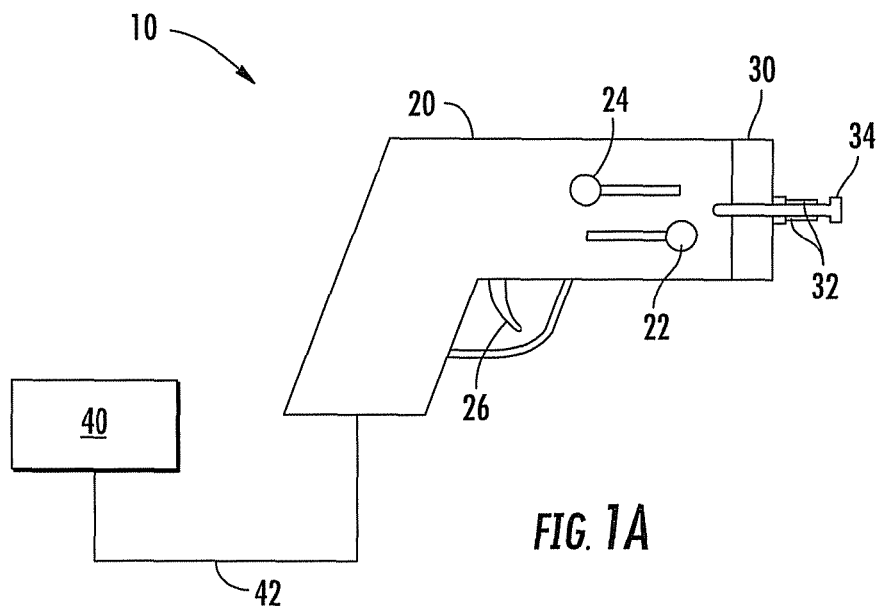
FIGS. 1A and 1B are side views of embodiments of a vasectomy instrument according to the presently disclosed subject matter.

The subject matter disclosed herein provides devices and methods for supplying energy for cauterizing a tubular vessel of a medical patient. Specifically, for example, the instrument and method can be used to ablate, coagulate, and/or otherwise block or close the vas deferens of a male patient. In one aspect illustrated for example only and without limitation in FIGS. 1A through 4, the subject matter disclosed herein provides a medically useful device or instrument, generally designated device 10 that can be used to perform a vasectomy procedure. Device 10 can comprise a hand piece, generally designated 20, and a tip portion, generally designated 30, that can be positioned at an operative end of hand piece 20. One or more probes 32 can extend from tip portion 30 and provide energy for a medical ablation procedure (e.g., a vasectomy procedure).

As shown in FIGS. 1A-4, probes 32 can constitute a bipolar electrode. Specifically, for example, probes 32 can be radio frequency ablation (RFA) probes configured to provide RF energy to a target tissue for ablation purposes. In one particular configuration, probes 32 can, for example and without limitation, be approximately 22 gauge in size and approximately 2 cm in length. Each of probes 32 can comprise an insulating sheath 33 along the length of probes 32 except for at an end distal from tip portion 30. Sheath 33 can prevent current from flowing between probes 32 other than at the exposed ends. As a result, the likelihood of inadvertent damage to tissue away from the operative end of probes 32 can be reduced.

Figure 1B:
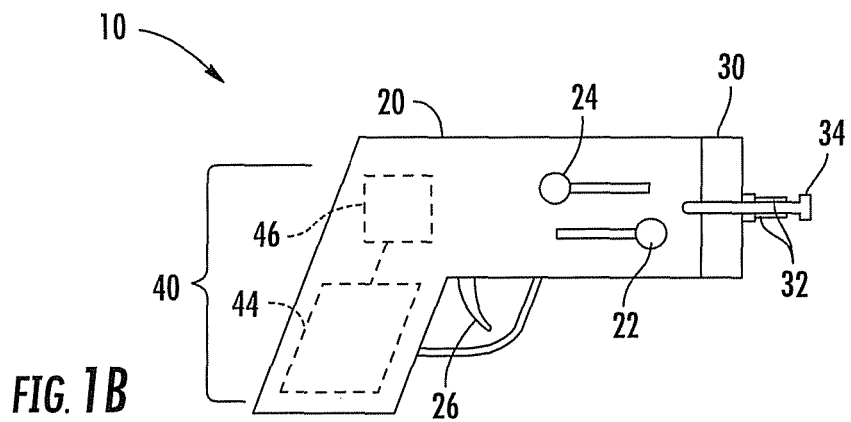
Figure 2:
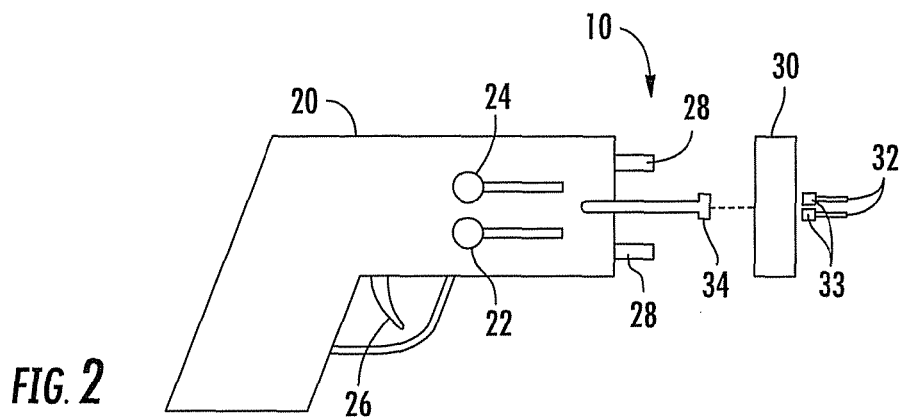
FIG. 2 is a side view of a vasectomy instrument with a tip portion detached from a hand piece according to an embodiment of the presently disclosed subject matter.
Figure 3:
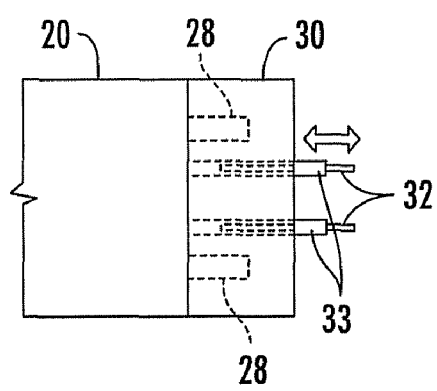
FIG. 3 a side view of a disposable tip of a vasectomy instrument according to an embodiment of the presently disclosed subject matter.
Figure 4:
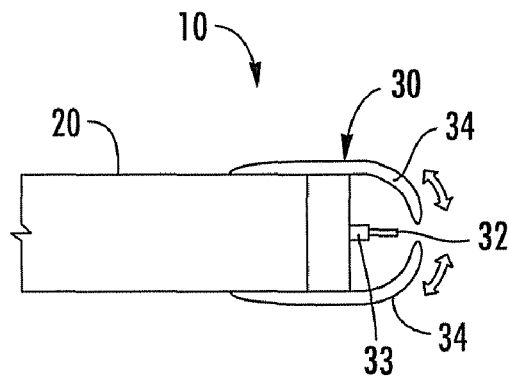
FIG. 4 is a top view of a vasectomy instrument according to an embodiment of the presently disclosed subject matter.

Probes 32 can be movable with respect to tip portion 30 such that probes 32 can be selectively extended relative to a surface of the tip portion to alternately conceal or expose probes 32. As shown in FIGS. 1 and 2, for example, probes 32 can be movable to retract into tip portion 30. To effect this movement, device 10 can comprise a probe position control, generally designated 22, on hand piece 20 that can be moved to correspondingly move probes 32. In particular, as shown in FIGS. 1A and 1B for example, probe position control 22 can be a slide button positioned on a side of hand piece 20 and movable towards tip portion 30 to extend probes 32 or away from tip portion 30 to retract probes 32. In this way, probes 32 can be moveable to a "stowed" position to protect probes 32 from damage, prevent contamination of probes 32, and/or prevent probes 32 from inadvertently piercing, scratching, or otherwise harming tissue before intended.

Device 10 can further comprise one or more grasping arms 34 that can extend from hand piece 20 beyond tip portion 30 and can be movable to grasp a target tissue and thereby hold the tissue in a position for probes 32 to act upon the target tissue. Specifically, grasping arms 34 can be configured to grasp a tubular vessel contained within a physical body. In the context of a vasectomy procedure, for example, grasping arms 34 can be configured to grasp a vas deferens of a male patient contained within the scrotum, thereby allowing probes 32 to ablate the vas.

Similarly to the control of the position of probes 32, the position of grasping arms 34 can likewise be adjusted by a control element. Namely, device 10 can comprise a grasper position control, generally designated 24, on hand piece 20 that can be moved to correspondingly move grasping arms 34. In particular, as shown in FIG. 1 for example, grasper position control 24 can be a second slide button positioned on a side of hand piece 20 and movable towards tip portion 30 to move grasper arms 34 towards each other (i.e., to grasp the vas) or away from each other (i.e., to release the vas). In this way, grasping arms 34 can be selectively movable to hold and stabilize the target tissue in a position for probes 32 to ablate the tissue.

Device 10 can be connected to a power supply 40, which can supply energy to probes 32. In one particular example, power supply 40 can be a radio frequency generator. Referring to FIG. 1A, device 10 can be connected to power supply 40 by a wire or cable 42. Those having ordinary skill in the art will recognize that power supply 40 can include a level control to regulate the power input supplied to probes 32. Alternatively, as shown in FIG. 1B, power supply 40 can comprise a power source 44 (e.g., a battery pack) and an RF generator 46 integrated into hand piece 20 to allow device 10 to be easily transported and operated without being tethered to a separate power supply. In either configuration, to activate probes 32, device 10 can comprise an actuator 26, which can be a trigger mechanism similar to that of a firearm as shown in FIGS. 1 and 2. Thus, by pulling actuator 26, the supply of energy from power supply 40 to probes 32 can be regulated.

In some configurations, tip portion 30 can be a disposable portion that can be selectively detachable from hand piece 20. As shown in FIG. 2, for example, hand piece 20 can comprise mounting posts 28 extending from an end thereof. Tip portion 30 can comprise complementary recesses configured to receive mounting posts 28 and align tip portion 30 with the end of hand piece 20 (i.e., to align mechanisms for movement of probes 32). In this configuration, device 10 can be used to perform a procedure on a medical patient, and once the procedure is completed, tip portion 30 can be detached from hand piece 20 and discarded. In this way, concerns regarding contamination between patients can be diminished, since probes 32 on a given tip portion 30 can be used for only a single patient. Stated otherwise, because only the ends of probes 32 are configured for non-superficially contacting a patient, hand piece 20 can be reused with new copies of tip portion 30 for subsequent patients. In addition, concerns regarding degradation of probes 32 or mechanical wearing issues can be substantially eliminated since probes 32 can be designed for single-use operation.

Figure 5:
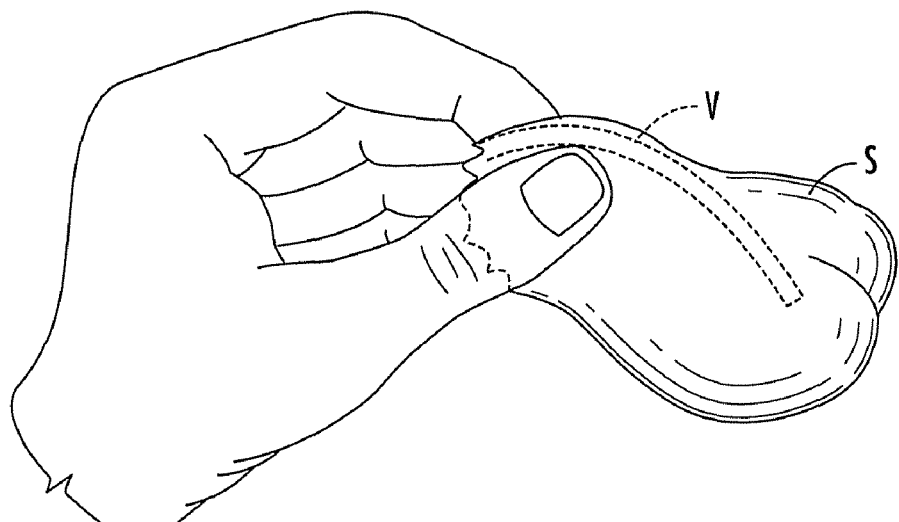
FIGS. 5, 6, 7A, and 7B are representations of steps in a vasectomy procedure according to an embodiment of the presently disclosed subject matter.

Regardless of the specific configuration of vasectomy device 10, vasectomy device 10 can be used for methods for performing a vasectomy as shown in FIGS. 5-7B. First, as shown in FIG. 5, a vas V of a patient can be grasped by the physician and brought up to a position just below the surface of scrotum S. For instance, such an arrangement can be achieved with the physician standing on one side of the patient while the patient is lying on an exam table. After cleaning the scrotum with an antibacterial liquid, a local anesthetic (e.g. 1% lidocaine) can be injected to produce a local skin anesthesia via a needle. As shown in FIG. 5, for example, this portion of the procedure can be performed while the physician is grasping vas V with his or her left hand.

Figure 6:
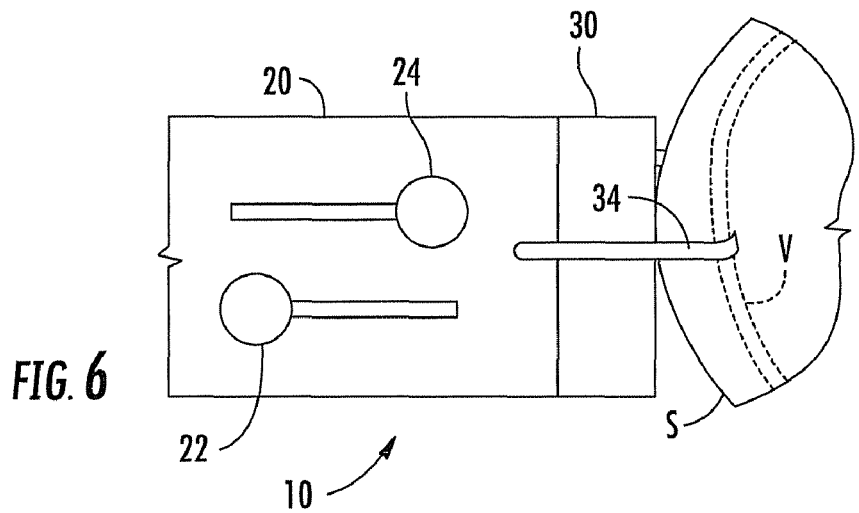
Figure 7A:
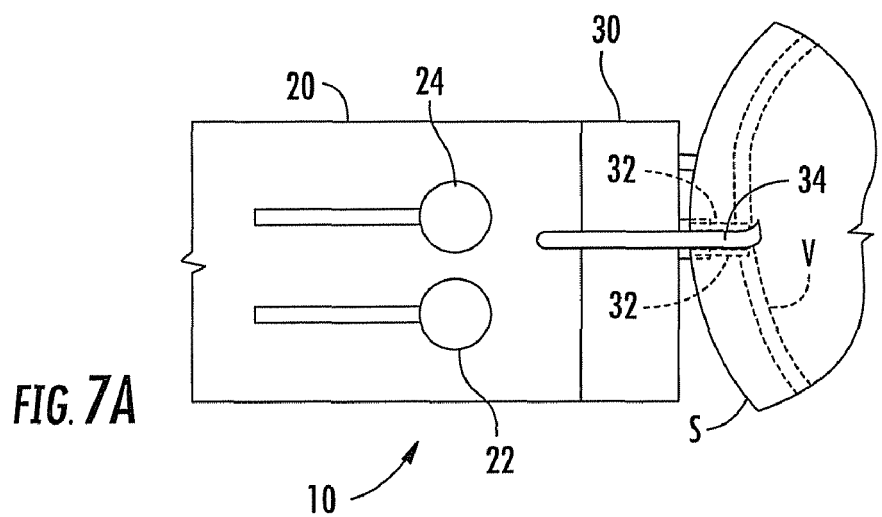
Figure 7B:
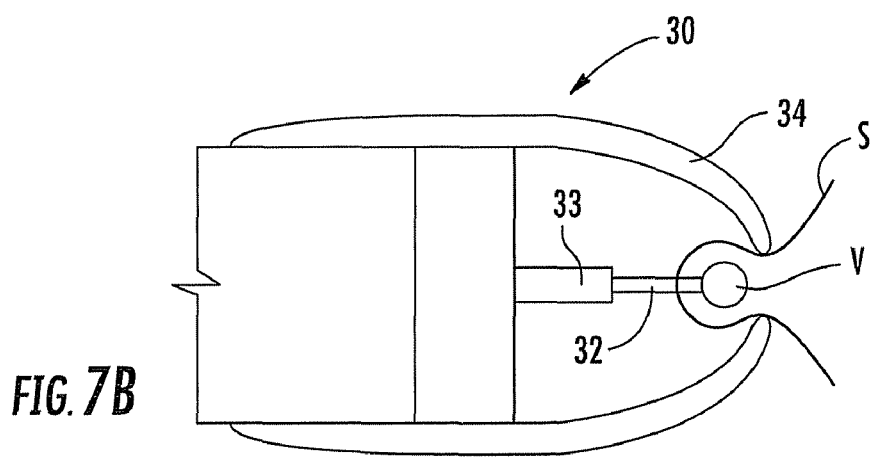

As shown in FIG. 6, after achieving local anesthesia, the physician can position instrument 10 with tip portion 30 adjacent to scrotum S (either directly against or merely near to scrotum S), with vas V immediately below the skin. From this position, the physician can actuate grasper position control 24 (e.g., slide grasper position control 24 towards scrotum S) to cause grasper arms 34 to encompass vas V, such as by constraining vas V between grasper arms 34. Alternatively, as shown in FIGS. 7A and 7B, grasper arms 34 can be configured to reach behind vas V to prevent vas V from receding back into scrotum S. In this way, grasper arms 34 can function not only to align and stabilize vas V but also hold vas V in place as pressure is applied by the extension of probes 32 against and/or into vas V.

With vas V stabilized in this manner, the physician can actuate probe position control 22 (e.g., slide probe position control 22 towards scrotum S) to extend probes 32. Device 10 can be particularly designed such that grasper arms 34 constrain vas V in a position that is aligned with probes 32. In this way, probes 32 can be extended into scrotum S (i.e., through the scrotal skin) to a position either immediately adjacent to and in contact with vas V or penetrating vas V as seen in FIGS. 7A and 7B.

After penetration of vas V by probes 32, the physician can provide energy to probes 32 to ablate, coagulate, or otherwise block or close vas V. For instance, where device 10 has the configuration shown in FIGS. 1A-4, the physician can operate actuator 26 to initiate a supply of energy (e.g., RF energy) to probes 32. As the energy moves from one of probes 32 to the other, cauterization of vas V occurs.

After adequate destruction and cauterization has occurred, actuator 26 can be released, causing cessation of the flow of energy to probes 32. At this point in the procedure, the physician can retract probes 32, such as by moving probe position control 22 (e.g., sliding probe position control 22 away from scrotum S), thereby allowing probes 32 to withdraw from within scrotum S. Grasper position control 24 can be moved (e.g., slid away from scrotum S) to release vas V from its grip. The entry points of probes 32 into scrotum S can be covered with antibiotic ointment to facilitate healing.

It is believed that the healing process with respect to this procedure can be dramatically shortened compared to typical procedures since the methods for using the devices described herein involve the creation of only two puncture entry wounds into the scrotum (after administration of local anesthesia via injection), and cauterization and destruction of vas V can be accomplished in a short time period. Accordingly, the present methods can be performed without surgical excision of a portion of vas V while still achieving the same desired effect of sterilization of the male.

The present subject matter can be embodied in other forms without departure from the spirit and essential characteristics thereof. The embodiments described therefore are to be considered in all respects as illustrative and not restrictive. For example, while discussion of the present subject matter is presented in regard to use in preforming male sterilization, it can be similarly applied in other related applications, such as cauterization of other tubular vessels or fallopian tubes. In this regard, although the present subject matter has been described in terms of certain preferred embodiments, other embodiments that are apparent to those of ordinary skill in the art are also within the scope of the present subject matter.

What is claimed is:

1. A device for cauterizing a tubular vessel comprising:
   a hand piece comprising one or more mounting posts extending from a surgically operative end of the hand piece;
   a tip portion selectively attachable to the hand piece by engaging with the one or more mounting posts at the surgically operative end of the hand piece;
   one or more grasping arms extending beyond the tip portion, the one or more grasping arms being movable to grasp a portion of the physical body in which the tubular vessel is contained that is positioned at or near the tip portion;
   one or more probes extending from the tip portion, the one or more probes being movable with respect to a surface of the tip portion such that the one or more probes can be selectively extended relative to the surface of the tip portion, the one or more probes being configured to puncture a physical body in which the tubular vessel is contained; and
   a power supply configured to supply energy to the one or more probes.

2. The device of claim 1, wherein the tip portion is a disposable portion designed for a single use.

3. The device of claim 1, wherein the one or more probes comprise two probes of a bipolar electrode.

4. The device of claim 1, further comprising a probe position control movable with respect to the hand piece, wherein movement of the probe position control correspondingly causes movement of the one or more probes with respect to the tip portion.

5. The device of claim 4, wherein the probe position control comprises a first slide button positioned on a side of the hand piece.

6. The device of claim 1, wherein the one or more grasping arms are connected to the tip portion.

7. The device of claim 1, further comprising a grasper position control movable with respect to the hand piece, wherein movement of the grasper position control correspondingly causes movement of the one or more grasping arms.

8. The device of claim 7, wherein the grasper position control comprises a second slide button positioned on a side of the hand piece.

9. The device of claim 1, wherein the target tissue comprises a vas deferens of a male.

10. The device of claim 1, wherein the power supply comprises a radio frequency energy generator configured for supplying radio frequency energy to the one or more probes.

11. The device of claim 10, wherein the power supply is incorporated into the hand piece.

12. The device of claim 1, further comprising an actuator configured to regulate the supply energy from the power supply to the one or more probes.

13. A device for cauterizing a tubular vessel comprising:
    a hand piece comprising a trigger-style actuator;
    a tip portion selectively connectable to a surgically operative end of the hand piece;
    one or more probes extending from the tip portion, the one or more probes being configured to puncture a physical body in which the tubular vessel is contained;
    one or more grasping arms connected to the tip portion and extending beyond the tip portion, the one or more grasping arms being movable to grasp a portion of the physical body in which the tubular vessel is contained that is positioned at or near the tip portion;
    a radio frequency energy generator integrated into the hand piece, the radio frequency energy generator being configured to supply radio frequency energy to the one or more probes upon actuation of the trigger mechanism such that the target tissue is ablated;
    wherein the hand piece comprises one or more mounting posts extending from the surgically operative end of the hand piece; and
    wherein the tip portion is selectively connectable to the hand piece by engaging with the one or more mounting posts.

14. A method for cauterizing a tubular vessel, the method comprising:
    providing a device comprising a hand piece, a tip portion provided at a surgically operative end of the hand piece, one or more probes extending from the tip portion, and one or more grasping arms extending beyond the tip portion;
    positioning the device near to or against a physical body containing a tubular vessel;
    grasping a portion of the physical body containing the tubular vessel using the one or more grasping arms;
    puncturing the portion of the physical body in which the tubular vessel is contained with the one or more probes;
    moving the one or more probes into contact with the tubular vessel; and
    after puncturing the portion of the physical body and moving the one or more probes into contact with the tubular vessel, providing energy to the one or more probes to cauterize the tubular vessel.

15. The method of claim 14, wherein the physical body comprises a scrotum and the tubular vessel comprises a vas deferens of a male.

16. The method of claim 14, wherein the tip portion is selectively removable from the hand piece, wherein providing a device comprises attaching the tip portion to the hand piece.

17. The method of claim 14, wherein providing energy to the one or more probes comprises providing radio frequency energy to the one or more probes.

18. The method of claim 14, wherein providing energy to the one or more probes comprises connecting the one or more probes to a power supply.

19. The method of claim 14, comprising retracting the probes out of contact with the tubular vessel after providing energy to the one or more probes to cauterize the tubular vessel.

* * * * *